US012661208B2

(12) United States Patent
Friend et al.

(10) Patent No.: US 12,661,208 B2
(45) Date of Patent: Jun. 23, 2026

(54) PASSIVE IDENTIFICATION FOR LIMITED-USE SURGICAL DEVICES AND LIMITED-USE DISPOSABLE ATTACHMENTS

(71) Applicant: Medtronic Xomed, LLC, Jacksonville, FL (US)

(72) Inventors: Matthew J. Friend, Jacksonville, FL (US); Bo D. Turano, Jacksonville, FL (US)

(73) Assignee: Medtronic Xomed LLC, Minneapolis, MN (US)

( * ) Notice: Subject to any disclaimer, the term of this patent is extended or adjusted under 35 U.S.C. 154(b) by 0 days.

(21) Appl. No.: 18/761,960

(22) Filed: Jul. 2, 2024

(65) Prior Publication Data

US 2025/0025261 A1      Jan. 23, 2025

Related U.S. Application Data

(60) Provisional application No. 63/527,653, filed on Jul. 19, 2023.

(51) Int. Cl.
A61B 17/16          (2006.01)
A61B 17/32          (2006.01)
(Continued)

(52) U.S. Cl.
CPC .......... A61B 90/98 (2016.02); A61B 17/1626 (2013.01); A61B 17/1628 (2013.01);
(Continued)

(58) Field of Classification Search
CPC ............ A61B 17/1626; A61B 17/1628; A61B 17/32002; A61B 90/98; A61B 2017/0023; A61B 2017/00473
(Continued)

(56) References Cited

U.S. PATENT DOCUMENTS 5,618,293 A      4/1997 Sample et al.
5,685,838 A      11/1997 Peters et al.
(Continued)

FOREIGN PATENT DOCUMENTS

EP            0303436 A1      2/1989
EP            0669105 A2      8/1995
(Continued)

OTHER PUBLICATIONS

Extended European Search Report EP23193270.8 dated Jan. 15, 2024, 6pp.
(Continued)

*Primary Examiner* — Jessica Weiss
(74) *Attorney, Agent, or Firm* — Carter, DeLuca & Farrell LLP

(57)                    ABSTRACT

A surgical system includes an integrated power console configured to power a motor of a cutting device and monitor feedback from during use to indicate the condition of the motor. The system includes a disposable cutting tool having a shaft engageable within the cutting device and supporting a cutting head for rotation with the shaft to cut tissue or bone. The disposable cutting tool includes: a shaft assembly configured to lock the disposable cutting tool onto the cutting device; a proximal connector configured to align the shaft with an output shaft of the motor; and one or more components that presents a unique identification property for tool identification and/or erodes during a sterilization process to negatively affect rotation of the shaft such that the user can identify or the IPC alerts the user that the disposable cutting tool is compromised and needs to be replaced.

11 Claims, 6 Drawing Sheets

(51) Int. Cl.
   *A61B 90/90*        (2016.01)
   *A61B 90/98*        (2016.01)
   *A61B 17/00*        (2006.01)
(52) U.S. Cl.
   CPC .................. *A61B 17/32002* (2013.01); *A61B 2017/0023* (2013.01); *A61B 2017/00473* (2013.01)
(58) Field of Classification Search
   USPC ...................................................... 606/80–85
   See application file for complete search history.

(56)                  References Cited

U.S. PATENT DOCUMENTS

| | | |
|---|---|---|
| 5,957,881 A | 9/1999 | Peters et al. |
| 6,007,556 A | 12/1999 | Kablik et al. |
| 6,293,957 B1 | 9/2001 | Peters et al. |
| 6,645,218 B1 | 11/2003 | Cassidy et al. |
| 6,824,552 B2 | 11/2004 | Robison et al. |
| 7,077,845 B2 | 7/2006 | Hacker et al. |
| 7,244,263 B2 | 7/2007 | Robison et al. |
| 7,674,263 B2 | 3/2010 | Ryan |
| 7,699,846 B2 | 4/2010 | Ryan |
| 7,719,437 B2 | 5/2010 | Bertram, III |
| 7,803,170 B2 | 9/2010 | Mitusina |
| 7,854,736 B2 | 12/2010 | Ryan |
| 7,942,880 B2 | 5/2011 | Bertram, III |
| 7,993,360 B2 | 8/2011 | Hacker et al. |
| 8,052,706 B2 | 11/2011 | Mitusina |
| 8,057,500 B2 | 11/2011 | Mitusina |
| 8,142,464 B2 | 3/2012 | Mitusina |
| 8,366,559 B2 | 2/2013 | Papenfuss et al. |
| 8,808,375 B2 | 8/2014 | Bertram, III |
| 8,852,191 B2 | 10/2014 | Bertram, III |
| 8,870,893 B2 | 10/2014 | Makower et al. |
| 8,944,926 B2 | 2/2015 | Kramer et al. |
| 9,198,685 B2 | 12/2015 | Edwards et al. |
| 9,381,032 B2 | 7/2016 | Edwards et al. |
| 9,474,541 B2 | 10/2016 | Zider et al. |
| 9,486,232 B2 | 11/2016 | Heisler et al. |
| 9,517,076 B2 | 12/2016 | Papenfuss |
| 9,603,607 B2 | 3/2017 | Papenfuss |
| 9,668,751 B2 | 6/2017 | Papenfuss |
| 9,775,967 B2 | 10/2017 | Hatta et al. |
| 9,808,867 B2 | 11/2017 | Krause et al. |
| 9,833,249 B2 | 12/2017 | Bertram, III |
| 9,839,441 B2 | 12/2017 | Hayes et al. |
| 10,179,002 B2 | 1/2019 | Wasicek et al. |
| 10,271,830 B2 | 4/2019 | Papenfuss et al. |
| 10,492,800 B2 | 12/2019 | Papenfuss |
| 10,524,820 B2 | 1/2020 | Algawi et al. |
| 10,743,912 B2 | 8/2020 | Papenfuss |
| 10,779,806 B2 | 9/2020 | Kieturakis et al. |
| 11,020,139 B2 | 6/2021 | Curtin et al. |
| 11,064,980 B2 | 7/2021 | Papenfuss et al. |
| 11,065,012 B2 | 7/2021 | Edwards |
| 2002/0165549 A1* | 11/2002 | Owusu-Akyaw ........................... A61B 17/1633 606/80 |
| 2009/0270812 A1 | 10/2009 | Litscher |
| 2011/0077664 A1 | 3/2011 | Schulz et al. |
| 2011/0224577 A1 | 9/2011 | Park |
| 2011/0313326 A1 | 12/2011 | Johansen |
| 2012/0116404 A1* | 5/2012 | Harp .................. A61B 17/1671 606/85 |
| 2015/0327880 A1* | 11/2015 | Wasicek ........... A61B 17/32002 606/115 |
| 2015/0327881 A1 | 11/2015 | Willhite et al. |
| 2019/0357924 A1 | 11/2019 | Papenfuss |
| 2021/0282799 A1 | 9/2021 | Curtin et al. |
| 2022/0015821 A1 | 1/2022 | Norton et al. |
| 2022/0039886 A1* | 2/2022 | Dumpe .................. G16H 10/60 |
| 2022/0054161 A1* | 2/2022 | Mayer ........... A61B 17/320068 |
| 2022/0133360 A1 | 5/2022 | Papenfuss et al. |
| 2022/0241045 A1* | 8/2022 | Carusillo ........... A61B 17/1615 |

FOREIGN PATENT DOCUMENTS

| | | | |
|---|---|---|---|
| EP | 0917446 B1 | 4/2005 | |
| WO | 2015133006 A1 | 9/2015 | |
| WO | WO-2018140646 A1 * | 8/2018 | ............. A61B 34/25 |

OTHER PUBLICATIONS

Partial European Search Report EP23193260.9 dated Jan. 15, 2024, 15pp.
Extended European Search Report EP23193260.9 dated Apr. 9, 2024, 16pp.
International Search Report and Written Opinion, PCT/IB2024/056926, dated Jan. 2, 2025, 17pp.

* cited by examiner

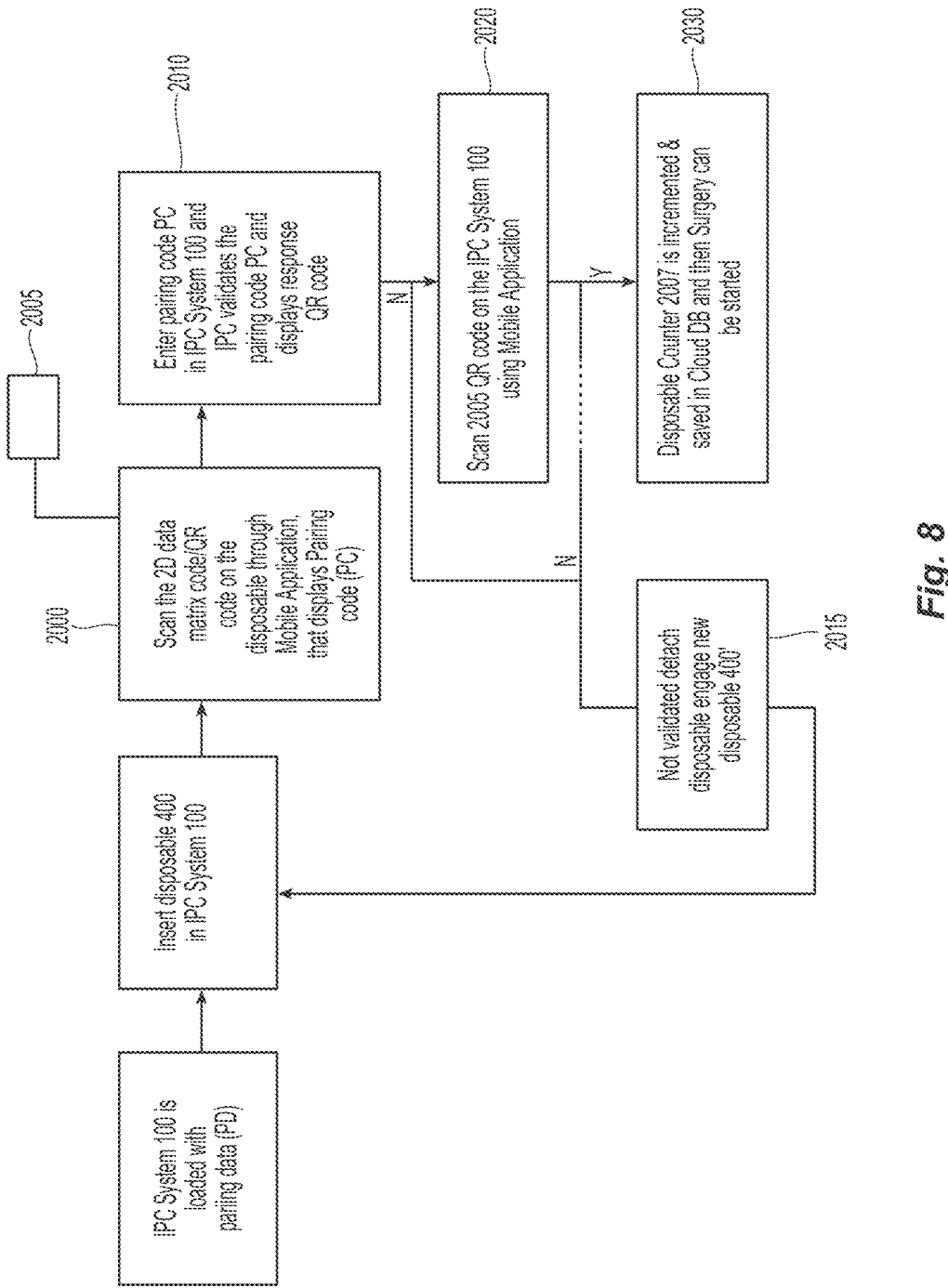

*Fig. 8*

IPC System 100 is loaded with pairing data (PD)

Insert disposable 400 in IPC System 100

Scan the 2D data matrix code/QR code on the disposable through Mobile Application, that displays Pairing code (PC) — 2000

2005

Enter pairing code PC in IPC System 100 and IPC validates the pairing code PC and displays response QR code — 2010

N

Scan 2005 QR code on the IPC System 100 using Mobile Application — 2020

N

Not validated detach disposable engage new disposable 400 — 2015

Y

Disposable Counter 2007 is incremented & saved in Cloud DB and then Surgery can be started — 2030

PASSIVE IDENTIFICATION FOR LIMITED-USE SURGICAL DEVICES AND LIMITED-USE DISPOSABLE ATTACHMENTS

CROSS-REFERENCE TO RELATED APPLICATION

This application claims the benefit of and priority to U.S. Provisional Patent Application No. 63/527,653 filed Jul. 19, 2023, the entire disclosure of which is incorporated by reference herein.

FIELD

The present disclosure relates to limited-use surgical devices and disposable attachments and surgical tools for use with surgical devices. More particularly, the present disclosure relates to surgical devices and/or attachments for use with surgical devices that are designed for, authenticated, or otherwise permitted for a limited number of surgical applications.

BACKGROUND

Powered surgical cutting devices and systems are utilized in a wide variety of surgical procedures to perform various different surgical cutting functions including, for example, drilling, tapping, resection, dissection, debridement, shaving, sawing, pulverizing, and/or shaping of anatomical tissue including bone.

Many of such powered surgical cutting devices and systems are precisely designed to ensure the devices function safely and effectively. However, regardless of the precision of design, all powered surgical devices and systems have components that tend to wear over prolonged use or in cases of excessive use increasing the risk of device failure. As a result, using a surgical device repeatedly for multiple surgical applications can increase the risk of device failure. Designing a limited-use surgical device that is disposable or designing a limited-use attachment for a surgical device that is disposable substantially mitigates this risk as a new, reliable instrument or attachment is utilized for each surgical application.

SUMMARY

As used herein, the term "distal" refers to the portion that is being described which is farther from an operator (whether a human surgeon or a surgical robot), while the term "proximal" refers to the portion that is being described which is closer to the operator. Terms including "generally," "about," "substantially," and the like, as utilized herein, are meant to encompass variations, e.g., manufacturing tolerances, material tolerances, use and environmental tolerances, measurement variations, design variations, and/or other variations, up to and including plus or minus 10 percent. To the extent consistent, any of the aspects described herein may be used in conjunction with any or all of the other aspects described herein. As used herein "limited-use" may refer to a specified number of surgical uses of a surgical device based on empirical evidence, based on feedback, or "limited use" may refer to a single use.

Provided in accordance with aspects of the present disclosure is a surgical system for a cutting device which includes an integrated power console (IPC) configured to power a motor of a cutting device and monitor feedback from one or more indicators during use over time to indicate the condition of the motor. The system also includes a disposable cutting tool having an elongated shaft operably engageable within the cutting device and supporting a cutting head at a distal end thereof such that rotation of the elongated shaft and the cutting head cuts tissue or bone. The disposable cutting tool includes: a shaft assembly configured to operably engage and selectively lock the disposable cutting tool onto the cutting device; a proximal connector configured to operably align and engage the elongated shaft of the disposable cutting tool with an output shaft of the motor; and one or more components disposed therein that erode during a sterilization process affecting rotation of the shaft.

Upon engagement of the disposable cutting tool with the cutting device and initial use, the negative feedback relative to the rotation of the elongated shaft is analyzed by the IPC and the user is notified that the disposable cutting tool is compromised and needs to be replaced.

In aspects according to the present disclosure, the one or more components include one or more seals disposed within the shaft assembly or the proximal connector configured to support the elongated shaft. In other aspects according to the present disclosure, the one or more seals are made from a material that erodes during a sterilization process such that the elongated shaft becomes imbalanced as the elongated shaft rotates within the respective shaft assembly or the proximal shaft connector upon re-use.

In aspects according to the present disclosure, the one or more seals are made from a material that erodes during a sterilization process such that fluid or air leaks from the respective shaft assembly or the proximal shaft connector upon re-use.

In aspects according to the present disclosure, the one or more components include one or more seals disposed about the shaft assembly configured to support an irrigation hub configured to introduce fluid atop the elongated shaft for transportation along the elongated shaft to the cutting head, wherein the one or more seals are made from a material that erodes during the sterilization process such that fluid leaks from the elongated shaft assembly upon re-use.

In aspects according to the present disclosure, the one or more components include one or more seals disposed within the proximal connector configured to operably align the elongated shaft of the disposable cutting tool with the output shaft of the motor, wherein the one or more seals are made from a material that erodes during the sterilization process such that suction leaks from the proximal connector upon re-use.

In aspects according to the present disclosure, the one or more seals include a geometry that erodes to impede rotation of the shaft which is communicated back to the IPC via one or more electrical parameters to prevent re-use of the disposable cutting tool. In other aspects according to the present disclosure, the one or more seals include a geometry that erodes to impede rotation of the shaft to about 90% or less or to an amount in which the IPC determines the cutting tool is unsafe for use and prohibits power to the tool.

Provided in accordance with aspects of the present disclosure is a cutting device including a housing having a motor disposed therein. A disposable cutting tool including an elongated shaft is operably engageable within the cutting device, the elongated shaft supporting a cutting head at a distal end thereof such that rotation of the elongated shaft and the cutting head cuts tissue or bone. The disposable cutting tool includes: a shaft assembly configured to operably engage and selectively lock the disposable cutting tool onto the cutting device; a proximal connector configured to operably align and engage the elongated shaft of the disposable cutting tool with an output shaft of the motor; and one or more components disposed within the disposable cutting tool that erode during a sterilization process effecting rotation of the elongated shaft. The one or more seals are made from a material that erodes during a sterilization process such that fluid or air leaks from the respective shaft assembly or the proximal shaft connector upon re-use.

In aspects according to the present disclosure, the one or more components include one or more seals disposed about the shaft assembly configured to support an irrigation hub configured to introduce fluid atop the elongated shaft for transportation along the elongated shaft to the cutting head, wherein the one or more seals are made from a material that erodes during the sterilization process such that fluid leaks from the elongated shaft assembly upon re-use.

In aspects according to the present disclosure, the one or more components include one or more seals disposed within the proximal connector configured to operably align the elongated shaft of the disposable cutting tool with the output shaft of the motor, wherein the one or more seals are made from a material that erodes during the sterilization process such that suction leaks from the proximal connector upon re-use.

In aspects according to the present disclosure, the one or more seals include a geometry that erodes to impede rotation of the shaft about 90% or less or to an amount in which the IPC determines the cutting tool is unsafe for use and prohibits power to the tool.

Provided in accordance with other aspects of the present disclosure is a surgical system for a cutting device which includes an integrated power console (IPC) configured to power a motor of a cutting device and monitor feedback from one or more indicators during use over time to indicate the condition of the motor, the IPC including a database of disposable cutting tools and associated operating and safety parameters. A disposable cutting tool including an elongated shaft is operably engageable within the cutting device and supports a cutting head at a distal end thereof such that rotation of the elongated shaft and the cutting head cuts tissue or bone. The disposable cutting tool includes: a shaft assembly configured to operably engage and selectively lock the disposable cutting tool onto the cutting device; a proximal connector configured to operably align and engage the elongated shaft of the disposable cutting tool with an output shaft of the motor; and a coupling disposed within the shaft assembly and configured to operably engage the shaft assembly and the proximal connector, at least a portion of an inner peripheral surface of the coupling made from a material configured to contact the elongated shaft such that upon engagement of the disposable cutting tool with the cutting device and during initialization, the IPC transmits and receives one or more electricals signals from the shaft enabling the IPC to identify the disposable cutting tool from a database and configure operating and safety parameters particular to the disposable cutting tool.

In aspects according to the present disclosure, the contact geometry of the inner peripheral surface of the coupling varies to create a unique electrical ID for each disposable cutting tool. In other aspects according to the present disclosure, the amount of material in contact with the shaft varies to create a unique electrical ID for each disposable cutting tool.

In aspects according to the present disclosure, the type of material in contact with the shaft varies to create a unique electrical ID for each disposable cutting tool.

In aspects according to the present disclosure, the contact geometry of the inner peripheral surface of the coupling includes a series of annular rings to create a unique electrical ID for each disposable cutting tool.

In aspects according to the present disclosure, the contact geometry of the inner peripheral surface of the coupling includes one or more flanges that extend along the coupling parallel to the shaft to create a unique electrical ID for each disposable cutting tool. In other aspects according to the present disclosure, the flanges are arranged 90° relative to one another.

Provided in accordance with other aspects of the present disclosure is a method of identifying a disposable cutting tool for use with a surgical system which includes coupling a cutting device to an integrated power console (IPC) configured to power a motor disposed within the cutting device, the IPC configured to monitor feedback from one or more indicators during use over time to indicate the condition of the motor, the IPC including a database of disposable cutting tools and associated operating and safety parameters. The method also includes: engaging a disposable cutting tool including an elongated shaft within the cutting device, the disposable cutting tool including a cutting head disposed at a distal end thereof configured to cut tissue or bone upon rotation of the elongated shaft, wherein engaging the disposable cutting tool includes: operably engaging and selectively locking a shaft assembly onto the cutting device; operably aligning and engaging a proximal connector of the elongated shaft with an output shaft of the motor; and operably engaging a coupling disposed within the shaft assembly with the proximal connector, at least a portion of an inner peripheral surface of the coupling made from a material configured to contact the elongated shaft such that upon engagement of the disposable cutting tool with the cutting device and during initialization, the IPC transmits and receives one or more electricals signals from the shaft enabling the IPC to identify the disposable cutting tool from a database and configure operating and safety parameters particular to the disposable cutting tool.

In aspects according to the present disclosure, the method further includes varying the contact geometry of the inner peripheral surface of the coupling to create a unique electrical ID for each disposable cutting tool. In other aspects according to the present disclosure, varying the contact geometry includes adjusting the amount of material in contact with the shaft to create a unique electrical ID for each disposable cutting tool. In yet other aspects according to the present disclosure, varying the contact geometry includes adjusting the type of material in contact with the shaft to create a unique electrical ID for each disposable cutting tool. In still other aspects according to the present disclosure, varying the contact geometry includes a series of annular rings to create a unique electrical ID for each disposable cutting tool.

In aspects according to the present disclosure, varying the contact geometry includes one or more flanges that extend along the coupling parallel to the shaft to create a unique electrical ID for each disposable cutting tool. In other aspects according to the present disclosure, the method further includes arranging the flanges 90° relative to one another to create a unique electrical ID for a disposable cutting tool.

Provided in accordance with other aspects of the present disclosure is a method of identifying a disposable cutting tool for use with a surgical system which includes:

a) coupling a cutting device to an integrated power console (IPC) configured to power a motor disposed within the cutting device, the IPC configured to monitor feedback from one or more indicators during use over time to indicate the condition of the motor, the IPC including a database of disposable cutting tools and associated operating and safety parameters;

b) engaging an initial disposable cutting tool including an elongated shaft within the cutting device, the initial disposable cutting tool including a cutting head disposed at a distal end thereof configured to cut tissue or bone upon rotation of the elongated shaft, wherein engaging the initial disposable cutting tool includes:

operably engaging and selectively locking a shaft assembly onto the cutting device;

operably aligning and engaging a proximal connector of the elongated shaft with an output shaft of the motor; and operably engaging a coupling disposed within the shaft assembly with the proximal connector, an inner peripheral surface of the coupling including a geometry configured to contact the elongated shaft such that upon engagement of the initial disposable cutting tool with the cutting device and during initialization, the IPC transmits and receives one or more electricals signals from the shaft enabling the IPC to identify the initial disposable cutting tool from a database and configure operating and safety parameters particular to the initial disposable cutting tool;

c) using the initial disposable cutting tool to cut tissue or bone;

d) disengaging the initial disposable cutting tool from the cutting device;

c) engaging a new disposable cutting tool within the cutting device;

f) repeating steps a) through c) with the new disposable cutting tool;

g) disengaging the new disposable cutting tool;

h) engaging a new disposable cutting tool or re-engaging a previously-used disposable cutting tool within the cutting device; and i) repeating steps a) through c) with the new or previously-used disposable cutting tool until surgical completion.

Provided in accordance with other aspects of the present disclosure is a method of counting the number of times a disposable cutting tool is utilized with any surgical system which includes:

a) at least one of verifying the existence of or loading pairing data (PD) into an integrated power console (IPC);

b) inputting via scanning, reading an RFID or manual inputting, identification information relating to a disposable cutting tool into the IPC to generate a pairing code (PC) on a remote device;

c) entering the PC into the IPC and waiting for the IPC to generate a response code validating the disposable cutting tool;

d) inputting the response code into the IPC; and e) incrementing a counter associated with the disposable cutting tool and saving counter information in a cloud database for future accessibility.

In aspects according to the present disclosure, if the disposable cutting tool is not validated in step c), the method further comprises detaching the disposable cutting tool from the cutting device and engaging a new disposable cutting tool with the cutting device and repeating at least steps b) and c).

In aspects according to the present disclosure, the input identification information includes at least one of a 2D data matrix code, QR code or Aztec code.

In aspects according to the present disclosure, the PC is displayed on a mobile communication device.

In aspects according to the present disclosure, the response code is at least one of a 2D Matrix code, Aztek code, or QR code. In other aspects according to the present disclosure, the response code is inputted into the IPC by scanning the response code into the IPC. In yet other aspects according to the present disclosure, the response code is displayed on the mobile communication device and inputted into the IPC from the mobile communication device.

In aspects according to the present disclosure, the response code is manually entered into the IPC.

In aspects according to the present disclosure, the IPC includes software configured to increment the counter and save the counter information in the cloud database for future accessibility.

In aspects according to the present disclosure, the IPC includes software that determines the validity of each disposable cutting tool based on the expected number of uses of each disposable cutting tool per surgery or per use.

Provided in accordance with other aspects of the present disclosure is a cutting device including a disposable cutting tool having an elongated shaft operably engageable within the cutting device and supporting a cutting head at a distal end thereof such that rotation of the elongated shaft and the cutting head cuts tissue or bone. The elongated shaft includes a proximal portion having a first geometric cross section. The disposable cutting tool includes: a shaft assembly configured to operably engage and selectively lock the disposable cutting tool onto the cutting device; a proximal connector configured to operably align and engage the elongated shaft of the disposable cutting tool with an output shaft of the motor; and a coupling disposed within the shaft assembly and configured to operably engage the shaft assembly and the proximal connector, at least a portion of an inner peripheral surface of the coupling including a second geometry configured to complement and slidingly receive the first geometry therein.

In aspects according to the present disclosure, the second geometry of the coupling engages the first geometry of the shaft in fluid-tight sealing relation therewith. In other aspects according to the present disclosure, the contact geometry of the inner peripheral surface of the coupling includes a series of annular rings.

In aspects according to the present disclosure, the contact geometry of the inner peripheral surface of the coupling includes one or more flanges that extend along the coupling parallel to the shaft. In other aspects according to the present disclosure, the flanges are arranged 90° relative to one another.

BRIEF DESCRIPTION OF THE DRAWINGS

The above and other aspects and features of the present disclosure will become more apparent in view of the following detailed description when taken in conjunction with the accompanying drawings wherein like reference numerals identify similar or identical elements.

FIG. 8 is a flow chart showing another contemplated method for identifying, authenticating, and/or tracking disposable cutting tools for use with surgical procedures.

DETAILED DESCRIPTION

Figure 1:
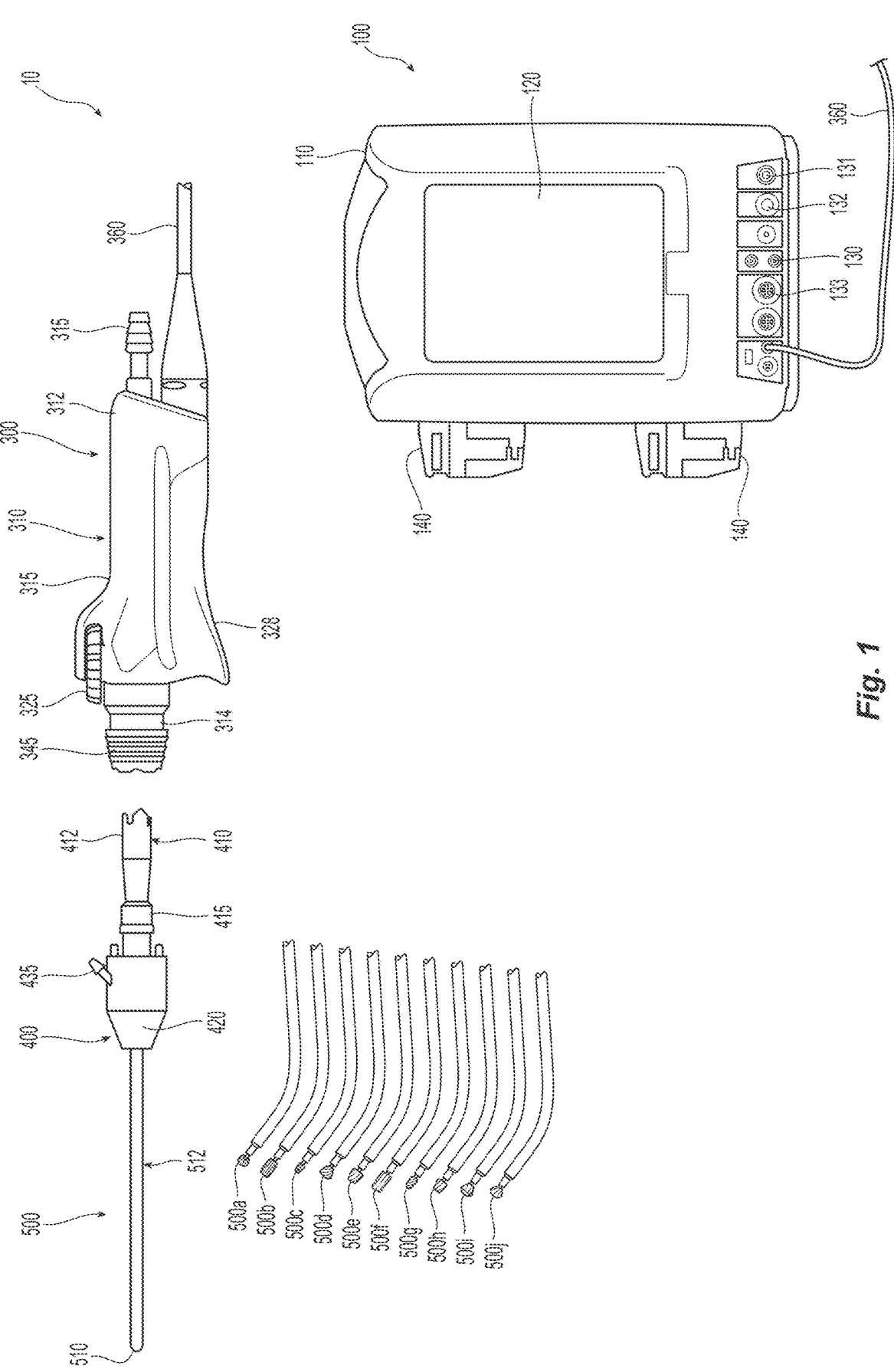
FIG. 1 is a perspective view of a surgical system in accordance with the present disclosure including a console and a powered surgical cutting device.

Turning to FIG. 1, a surgical system 10 provided in accordance with the present disclosure includes a console 100 and one or more surgical cutting devices 300. Console 100 may include an outer housing 110 enclosing the internal operable components of console 100, a touch screen graphical user interface (GUI) 120 to receive user input and display information to the user, a plurality of device ports 130-133 one or more fluid pumps 140, and/or other suitable features. One or more controllers including one or more processors and associated memory(s) are disposed within outer housing 110 and function to provide power and control signals to devices connected to console 100; to process user inputs, feedback data, and other data received at console 100; and to control the one or more fluid pumps 140. Suitable hardware and drive mechanisms as part of or in addition to controller may be disposed within outer housing 110 to perform the various functions of console 100 and may include, for example, one or more central processing units (CPU's) and/or microcontroller units (MCU's), power generating and control hardware and corresponding firmware/software stored thereon, sensor circuitry, motors, pump drivers, pump controllers, etc.

Figures 2, 3:
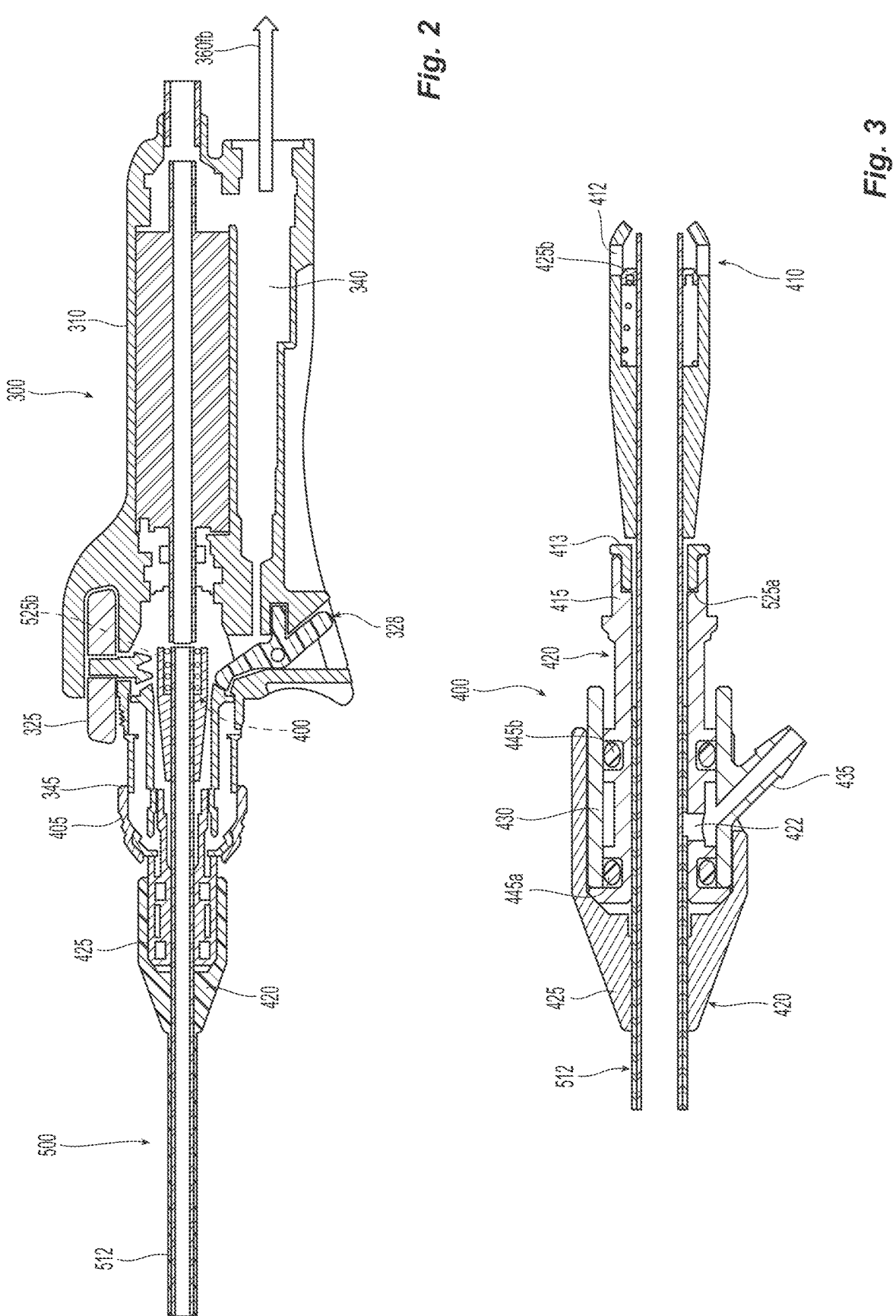
FIG. 2 is an internal, side view of a powered surgical cutting device for use with the system of FIG. 1 including a disposable cutting tool attached to a distal end thereof in accordance with one embodiment of the present disclosure.
FIG. 3 is an enlarged, internal side view of another embodiment of a disposable cutting tool for use with the surgical cutting device of FIG. 1.
Figure 5A:
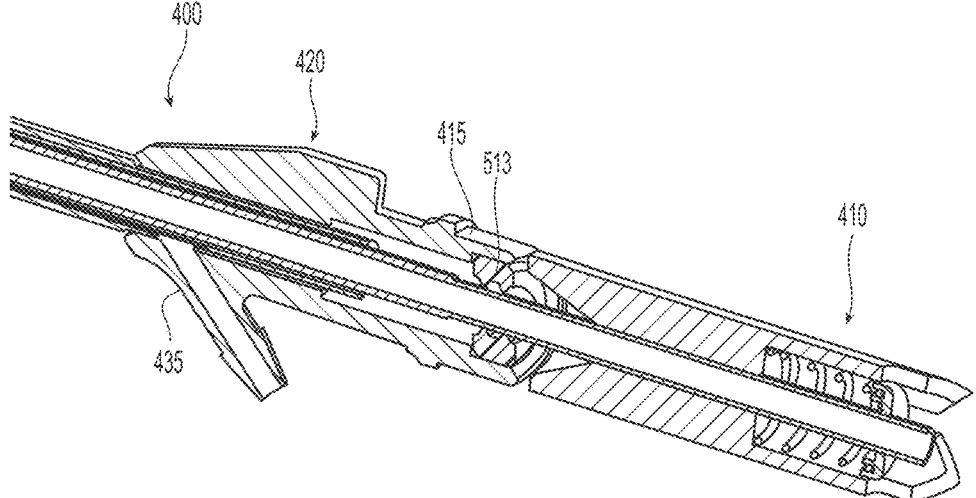
Figure 6A:
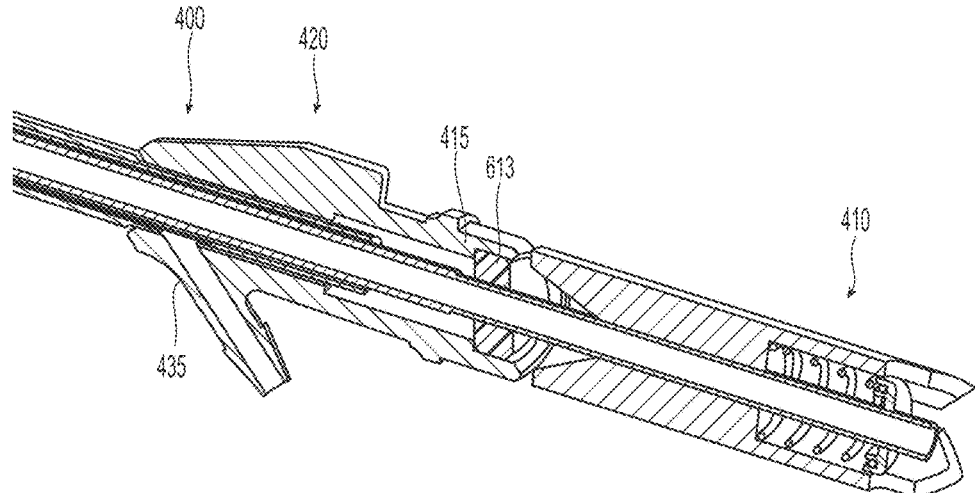

Turning now to FIGS. 1 and 2, the one or more surgical cutting devices 300 may define any suitable configurations for use in performing various different surgical tasks, for use in various different procedures, etc. One example of a suitable surgical cutting device, e.g., surgical cutting device 300, generally includes a housing 315, including proximal and distal ends 312, 314 which together define a gripping area commonly referred to herein as handle 310. Proximal end 312 is configured to electrically interface and mechanically engage a terminal end of a power cord 360 that connects to the console 100 which powers and monitors the cutting device 300 and other components disposed therein.

The distal end 314 of the housing 315 includes a locking collar 345 which is configured to mechanically engage and lock a disposable cutting tool 400 within the surgical cutting device 300 upon insertion therein. More particularly, the locking collar 345 is selectively movable between a first position facilitating insertion of the disposable cutting tool 400 within the distal end 314 of the housing 315 of the surgical device 300 and a second position wherein the locking collar 345 engages and locks a locking flange 415 disposed about the outer peripheral of the disposable cutting tool 400 within the housing 315 preventing removal (or disengagement from) of the disposable cutting tool 400 from the housing 315 until the locking collar 345 is moved back to the first position.

A locking mechanism 328 may be included to prevent accidental movement of the locking collar 345 during handling of the surgical cutting device 300. A rotating knob 325 may be included that operably couples to the outer shaft 512 and allows selective rotation of the disposable cutting tool 400 depending upon a particular purpose. Various examples of surgical cutting devices 300, cutting tools, rotating knobs 325, locking collars 345 are disclosed in commonly-owned U.S. patent application Ser. No. 17/810,427 and U.S. Pat. No. 10,881,427, the entire contents of both of which are incorporated by reference herein.

Disposable cutting tool 400 includes shaft assembly 420 which is configured to operably secure a shaft 512 of a surgical rotating or oscillating head 500, e.g., shaver or burr, having a specifically designed cutting head 510a-500j, rotational geometry, cutting geometry, angle relative the shaft 512 for accessing one or more surgical cavities (e.g., sinuses), etc. For the purposes here in, shaft 512 is generally described but includes the various internal inter-cooperating components operatively associated therewith. A proximal connector 410 of the disposable cutting tool 400 includes a proximal universal mechanical interface 412 which is operably configured to slidingly engage (e.g., via sliding receipt therein) the distal end 314 of housing 315 through locking collar 345 and mechanically and lock within housing 315 when locking collar 345 is disposed in the first position as described above (See FIG. 2). Locking mechanism 328 may be moved into position to prevent accidental removal of the shaft assembly 420 once engaged. One or more alignment features (not shown) may be utilized to ensure proper alignment of the shaft assembly 420 prior to mechanical engagement within housing 315 or to insure proper rotational features of the shaft assembly 420, cutting device 300, and head 500 are aligned prior to activation. Again, examples are disclosed in commonly-owned U.S. patent application Ser. No. 17/810,427 and U.S. Pat. No. 10,881, 427, the entire contents of both of which are incorporated by reference herein.

Shaft assembly 420 may also include an irrigation port 435 extending therefrom that is configured to operably connect to an irrigation source (not shown) configured to supply irrigation fluid to the distal end 510a-510j of the head 500, e.g., shaver or burr.

Turning in particular to FIG. 2, a motor 340 is disposed within handle 310 and is operably coupled via an array of mechanically-cooperating components (shown generically as components 350) to the proximal end mechanical interface 412 of the shaft assembly 420 to drive rotation and/or reciprocation of the shaft 512 to drive the head 510 to cut tissue or bone. Cord 360 connects motor 340 to console 100 to enable console 100 to power and control motor 340, thereby controlling the speed and other parameters of the shaft 512 as well as receiving feedback relating thereto. Motor 340 may be an electric motor, pneumatic motor, ultrasonic transducer, or other suitable motor configured to drive shaft 512 to rotate and/or reciprocate for cutting tissue or bone. Console 100 is configured to drive and control motor 340 such as, for example, a speed, torque, etc. output by motor 340. In aspects, surgical cutting device 300 may include additional features such as, for example, hand control(s), navigation, articulation, etc.

Turning briefly to FIG. 3, an internal view of the shaft assembly 420 is shown highlighting a distal cap 425 disposed at the distal end of the shaft assembly 420 which is configured to house an irrigation hub 430 therein having an irrigation port 435 extending proximally therefrom. As mentioned above, irrigation port 435 connects to an irrigation source (not shown) configured to supply irrigation fluid to the distal head 510 of the shaver or bur 500 to act as a coolant or to clear surgical debris. Irrigation hub 430, in turn, is defined to secure the shaft assembly 420 therein atop a pair of O-rings or seals 445*a* and 445*b* on either side of a fluid communication passage 422 defined within the shaft assembly 420 configured to deliver fluid from the irrigation port 435 to the shaft 512. Irrigation fluid is delivered under pressure along an outer periphery of the shaft 512 through passage 422. Shaft assembly 420 also includes a locking flange 415 which is configured to mechanically engage the locking collar 345 as described above.

Shaft 512 may include one or more O-rings or seals disposed at various points therealong which are configured to facilitate mechanical engagement and/or provide a fluid-tight seal between the shaft 512 and the shaft assembly 420 during rotation. For example, the locking flange 415 operably couples to the proximal connector 410 of the shaft assembly 420 via a mechanical seal/coupling 413. O-ring 525*a* provides a fluid-tight seal between seal/coupling 413 and locking flange 415. A second seal 525*b* may be disposed within the proximal connector 410 near proximal end mechanical interface 412 to insure a fluid-tight seal with the proximal end of the shaft 512.

By equipping all of the different cutting heads 510*a*-510*j* with a proximal universal mechanical interface 412, the surgeon can quickly interchange heads 510*a*-510*j* as needed during the course of the operation. During a typical resection procedure, anywhere from two-to-five (2-5) different cutting heads 510*a*-510*j* may be employed and interchanged repeatedly over the course of the operation. As can be appreciated, it is often difficult to keep track of the number of uses for each cutting head 510*a*-510*j* to gauge the expected performance expectancy of a particular cutting head, e.g., cutting head 510*a*, for subsequent use. Moreover, cutting heads 510*a*-510*j* and shaft assemblies 420 that are beyond their expected performance limitations or cutting heads 510*a*-510*j* and shaft assemblies 420 that are reprocessed or used off-label may perform far below a surgeon's expectations or become incompatible with electrical instrumentation and control software, e.g., or IPC 100.

Turning back to both FIGS. 2 and 3, one envisioned system to restrict the current cutting heads 510*a*-510*j* to single operation use, e.g., commonly referred to as "single-use", "disposable" or for use with a "reposable" instrument, would be to employ the information feedback system employed by the IPC in monitoring the feedback from the motor 340 during use of the cutting device 300. Put simply, when each disposable cutting tool 400 is attached and the motor 320 is activated, the IPC 100 monitors the feedback, e.g., current, voltage, vibration, etc., from the motor 320 during use and over time in a feedback loop to determine the condition of the surgical device 300 and, by default, the disposable cutting tool 400.

More particularly, in one aspect of the current disclosure, the unique aspects of the motor control feedback system employed by the IPC 100 may be utilized to not only monitor the system during use but also to initially identify the disposable cutting tool 400 upon initial engagement. Each disposable cutting tool 400 can be designed to communicate one or more parameters or a specific unique combination of parameters to the IPC 100 upon engagement to identify itself to the IPC 100 allowing the IPC 100 to either identify the disposable cutting tool 400, verify the disposable cutting tool 400, disavow the disposable cutting tool 400, flag the disposable cutting tool 400 or count the usage of the disposable cutting tool 400. If each disposable cutting tool 400 is identified by the IPC 100 when engaged prior to and/or during a given surgical procedure, the number of uses and the current condition of the disposable cutting tool 400 can be determined. Moreover, once identified, the IPC 100 can download power settings specific to the identified disposable cutting tool 400 for safe and efficient operation.

During sterilization and/or reprocessing, one or more of the O-rings or seals, e.g., 525*a* or 525*b*, may be subject to geometric conversion, erosion or expansion, affecting rotation of the shaft 512 when the cutting head, e.g., cutting head 510*a*, is identified and attached causing strain on the cutting head 510*a* which, in turn, causes the motor control feedback loop 360*fb* communicating with the console 100 (for example, forming part of one or more safety, monitoring, or control algorithms) to register an abnormal condition, e.g., a spike in current. If an abnormal condition is registered, the motor 320 is disabled until a new cutting head, e.g., cutting head 510*b* is attached and identified.

For example, if cutting head 510*a* is initially attached and during an initial identification check the current parameters of the cutting head 510*a* are compared to the last stored parameters of the cutting head 510*a*, a large current spike when initially engaging tissue would indicate that the disposable cutting tool 400 with that cutting head 510*a* had been reprocessed or sterilized for re-use.

Alternatively, one or more of the mechanically interfacing flanges, e.g., proximal flange 415 or irrigation hub 430, may be mounted atop an erodible component, affecting the alignment or balance of the flange 415 or hub 430 during engagement also affecting rotation of the shaft 512 which may also yield a similar conclusion and result in an abnormal condition that can be easily identified by the IPC 100.

For example, as mentioned above, an erodible seal 525*a* may be disposed between proximal locking flange 415 and seal/coupling 413 which when sterilized or reprocessed will affect the alignment and balance between components causing an abnormal condition identifiable by the IPC 100 during activation of the disposable cutting tool 400 with the sterilized cutting head 510*a*. Other similar scenarios are contemplated that would affect one or more feedback parameters that could be readily identified by the IPC 100 to alert the user of a reprocessed disposable cutting tool 400.

In another embodiment in accordance with the present disclosure, the seals 445*a* and 445*b* disposed on either side of the passage 422 in fluid communication with the irrigation port 435 may be made from a material susceptible to erosion when sterilized or reprocessed (or simply when exposed to ambient conditions for a prolonged period of time). If compromised, the deformation or erosion of the seals 445*a*, 445*b* may cause unacceptable degradation issues in performance such as an internal imbalance of the shaft assembly 420 (which may affect cutting window rotation) or severe irrigation leaks during use of the disposable cutting tool 400 with the cutting head 510*a* requiring replacement. Other seals, e.g., seal 525*a* (or possibly components), may be made from erodible materials and when sterilized or reprocessed deform causing performance degradation issues or irrigation leakage issues requiring replacement. A similar condition may occur with seal 525*b* disposed between the proximal connector 410 and shaft 512 which may cause intolerable suction leaks if the seal 525*b* is compromised due to sterilization or reprocessing.

As mentioned above, the geometry of the seals, e.g., seal 445a, 445b, 525a and 525b may be designed for geometric conversion during the sterilization or while being reprocessed. In other words, the seals 445a, 445b, 525a, and 525b may be designed to erode into a specific geometry or expand into a specific geometry when subject to a typical sterilization of reprocessing environment, e.g., heat or chemicals. As such, the geometry of the seals 445a, 445b, 525a and 525b at the end of the sterilization or reprocessing may greatly affect the alignment, balance, and/or seal of the internal components of the disposable cutting tool 400 and/or during rotation of the cutting head 510a affecting the fluid and suction integrity of the system during use.

In embodiment, the seals 445a, 445b, 525a and 525b may be designed to erode at a certain percentage that may trigger a default condition at the IPC 100, e.g., about 90% (or less) rotational efficiency of the shaft 512. Certain seal geometries may be engineered to erode to create a more severe imbalance in the shaft 512 to create a tactile condition even without the IPC 100 alert or feedback. In embodiments, other seals may be engineered to impede rotation of the shaft 512 to make the cutting device 300 virtually unusable. Feedback to the IPC 100 may be transmitted via electrical signals or current spikes due to strain or torque on the shaft 512 or motor 320.

Turning now to FIGS. 4A-6B, various embodiments of seal/coupling 413 geometries are shown for use as a replacement for seal/coupling 413 of FIG. 3 which are typically specified based on the geometry of the outer shaft 512 of the disposable cutting tool 400. The coupling geometries (hereinafter "seal 413, seal 513, and seal 613") shown seated within flange 415 of the shaft assembly 420 in FIGS. 4A, 5A and 6A, respectively, may be selectively engaged depending upon the geometry of the disposable cutting tool 400. In embodiments, a variety of seals having different geometries may be sold with the disposable tool 400 and one of the seals, e.g., seal 413, may be selectively engageable as part of a pre-assembly step prior to use depending on the geometry of the shaft 512 of the disposable cutting tool 400.

Figure 4A:
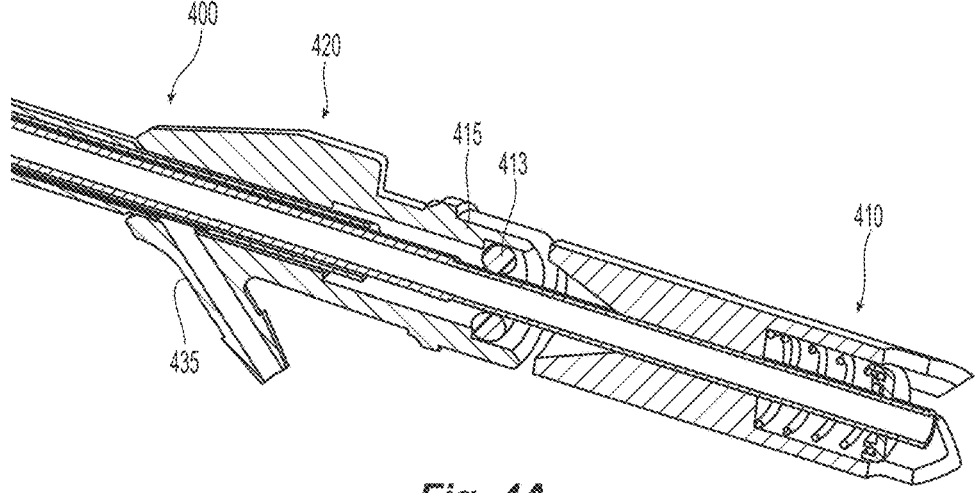
FIGS. 4A-6B show internal and perspective views of various embodiments of internal coupling that may be employed with a respective disposable cutting tool for identification purposes based on the unique geometric characteristics of each particular coupling.
Figure 4B:
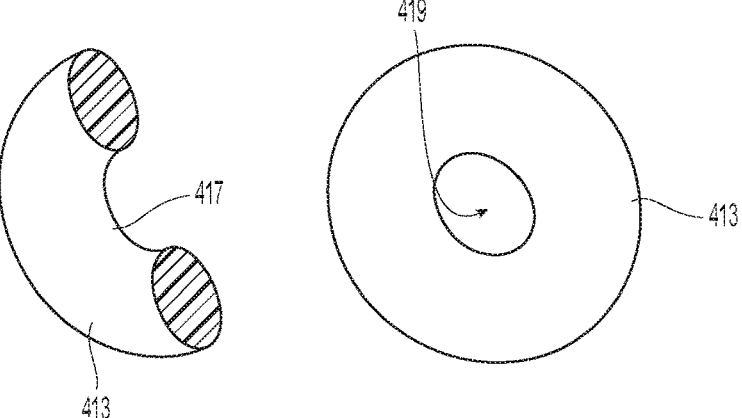
Figure 5B:
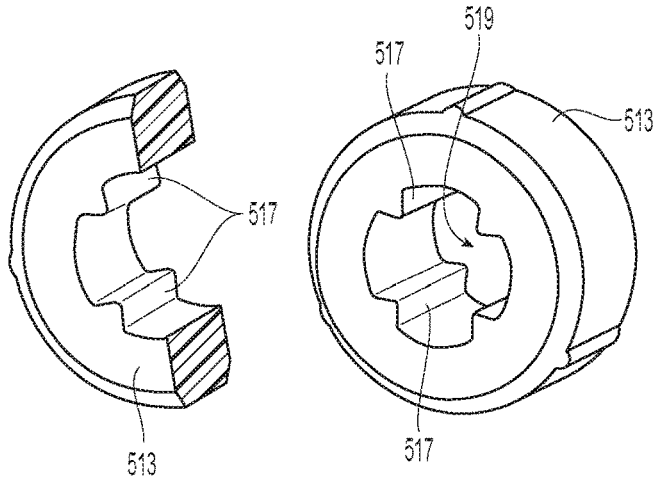
Figure 6B:
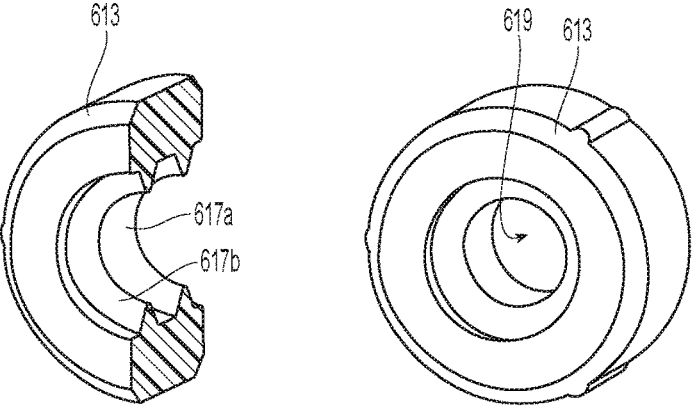

FIGS. 4B, 5B, and 6B show the respective seals 413, 513 and 613 each defining an inner aperture 419, 519, and 619 configured to receive the shaft 512 therethrough. As mentioned above, the inner peripheral surface of each aperture 419, 519, and 619 includes a specific geometry for receiving the shaft 512. For example, aperture 419 is donut-like and smooth and is configured to receive a shaft 512 having a relatively smooth outer periphery. Aperture 519 includes a series of flanges 517 that extend longitudinally along the inner peripheral surface of the aperture 519 forming a cross-like cross-section (e.g., flanges 517 at 90° relative to one another) and which is configured to receive a shaft 512 with a similar cross-sectional profile. Aperture 619 includes one or more annular rings 617a, 617b that run concurrently along the inner peripheral surface of the aperture 619 and which are configured to receive a shaft 512 with a similar cross-sectional profile.

As can be appreciated, the inner peripheral surfaces provide unique contact geometries relative to the shaft 512 to identify specific disposable cutting tools 400 based on a so-called "lock and key" type arrangement. Only a certain shaft 512 will fit a certain seal 413, 513 or 613.

In embodiments, this information can be communicated back to the IPC 100 when interrogated, e.g., upon engagement for safety or other reasons. By varying the geometry of the inner peripheral surfaces any number of different disposable cutting tools 400 may be cataloged in a library and the control parameters stored in the IPC 100 for setup and safety.

In other embodiments, the type of material or the amount of material in contact with the shaft 512 may create a unique electrical ID for each disposable cutting tool 400 that may be identified by the IPC 100. The outer peripheral surface may be composed of a silicone material and act as a seal while the inner peripheral surface (or a portion thereof) may communicate with the IPC 100 for ID purposes.

Figure 7:
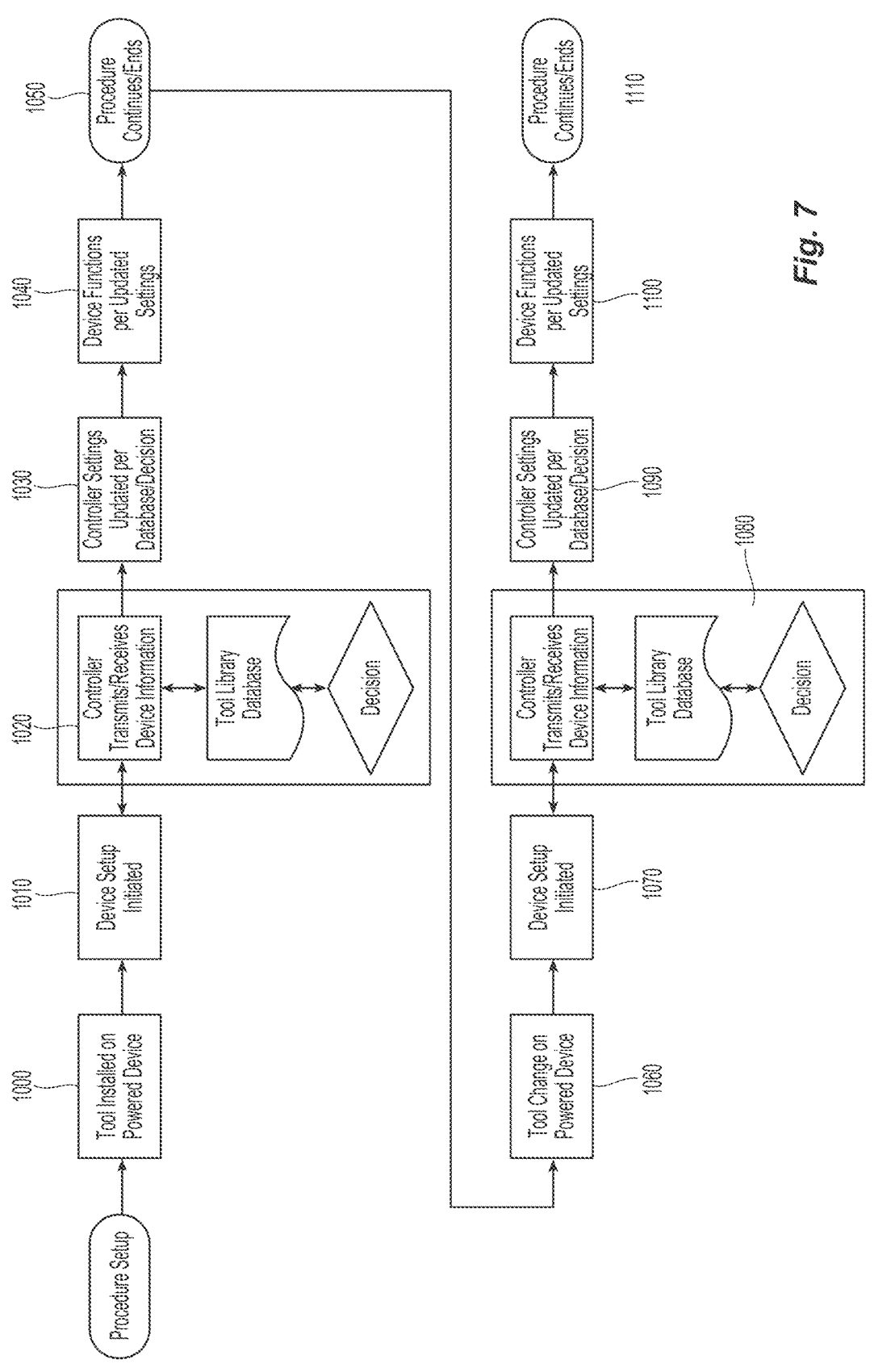
FIG. 7 is a flow chart showing one contemplated method for passively identifying a disposable cutting tool on the surgical cutting device in accordance with the present disclosure.

Turning briefly to FIG. 7 which shows one envisioned method for passively identifying a disposable cutting tool 400 on a cutting device 300 which an initial step 1000 of loading or installing the disposable cutting tool 400 onto the powered cutting device 300. In step 1010, the cutting device 300 is initialized. In step 1020, the IPC 100 transmits and receives device information from the cutting device 300 and disposable cutting tool 400 including contact information relating to the contact geometry of the seal 413 on the shaft 512, e.g., via electrical feedback through the shaft 512 and communicates with a tool library database to identify the disposable cutting tool 400.

In step 1030, once the disposable tool 400 is identified, one or more decisions are made relative to the disposable cutting tool 400 being verified as authentic, safe, and/or unexpired (not beyond the number of recommended uses), the disposable cutting tool's 400 operating and safety parameters are updated to the IPC 100. In step 1040, the cutting device 300 functions are tested per the updated settings. In step 1050, the surgical procedure is initiated.

If during a surgical procedure it is necessary to change out a disposable tool 400 either temporarily or entirely, the method continues with step 1060 wherein the current disposable cutting tool 400 is disengaged from cutting device 300 and either put aside or discarded and a substitute disposable cutting tool 400' is loaded with onto the powered cutting device 300. In step 1070, the cutting device 300 is initialized. In step 1080, the IPC 100 transmits and receives device information from the cutting device 300 and disposable cutting tool 400' including contact information relating to the contact geometry of the seal 413 on the shaft 512, e.g., via electrical feedback through the shaft 512 and communicates with the tool library database to identify the disposable cutting tool 400'.

In step 1090, once the disposable cutting tool 400' is identified, one or more decisions are made relative to the disposable cutting tool 400' being verified as authentic, safe, and/or unexpired, the disposable cutting tool's 400' operating and safety parameters are updated to the IPC 100. In step 1100, the cutting device 300 functions are tested per the updated settings with the new disposable cutting tool 400'. In step 1110, the surgical procedure is resumed.

As mentioned above, the re-use of single-use disposable tools remains one of the areas of concern for many manufacturers. Frustrating design efforts to curb reprocessing or unsanctioned additional tool usage is the fact that many of these single-use tools are designed to be used multiple times over the course of a given surgery (e.g., swapped-out) so traditional one-time engagement features and the like will not alleviate the issue.

Moreover, current IPC consoles are not connected to a network and are not designed to store data relating to any of the over 125 different disposables on the market relating to just ENT procedures alone. Moreover, the IPC 100 does not track the number of times a given disposable is used during a surgery nor the number of disposable cutting tools 400 used during a given surgery.

In one embodiment in accordance with the present disclosure, an application (e.g., mobile application) is designed and a method is utilized to identify, track and authenticate the number of times one or more disposable cutting tools 400 are used and/or used during surgery and for storing this information in the cloud to be remotely accessible from anywhere.

During the manufacturing of the disposable cutting tool 400, one or more surfaces of the disposable cutting tool 400 are encoded or marked in some fashion with one or more readable codes, e.g., a QR code, Aztek code, or other ID codes, that may be easily identifiable to the user or possible embedded, that is unique to that disposable cutting tool 400 and used for tracking purposes. The IPC 100 is uploaded with a QR code generator with pre-defined pairing data ("PD") and possibly minor GUI changes for compatibility purposes.

Turning briefly to FIG. 8, one envisioned method for identifying, authenticating, and/or tracking disposable cutting tools 400 for use with surgical procedure is shown and includes the following steps: Once the IPC 100 is uploaded with the pairing data PD and the disposable tool 400 is attached/inserted into the IPC 100, in step 2000, the 2D matrix code or QR code on the disposable cutting tool 400 is scanned by a scanning device 2005 to display a pairing code ("PC"), e.g., on a mobile device. In step 2010, the pairing code PC is entered into the IPC 100 to validate the pairing code PC against the pairing data PD in the IPC 100 related to the disposable cutting tool 400 and a QR response code is generated on the IPC console. In step 2020, the QR response code is scanned on the IPC 100 using the scanning device 2005. In step 2030, if validated, a counter 2007 associated with the disposable cutting tool 400 is incremented and saved in a database in the cloud and surgery may proceed. If not validated in step 2010, the IPC 100 will not authenticate the disposable cutting tool 400 and a different disposable cutting tool 400' must be substituted and the new disposable cutting tool 400' will need to be validated and paired starting with step 2000. As a result, disposable cutting tool 400 will need to be detached in step 2015 and a new disposable cutting tool 400' attached and inserted into the IPC 100 and the method returns to step 2000 above. In embodiments, a QR code may be generated in step 2010 that invalidates the disposable cutting tool 400 when read by a scanner in step 2020. At this point, the disposable cutting tool 400 is detached in step 2015 shown here in phantom line representation.

The history of each disposable cutting tool 400 or 400' is recorded and saved under the disposable tool's unique ID and, more importantly, is retrievable and verifiable by the IPC 100 according to the disposable cutting tool's 400 unique ID. Single-use disposable cutting tools 400 may be identified for reprocessing and re-use purposes and other disposable cutting tools 400 that have longer life expectancy over multiple surgical procedures may be tracked by the number of times each disposable cutting tool 400 is used during a single surgical procedure or over multiple surgical procedures.

One or more algorithms may be utilized to estimate the wear of a disposable cutting tool 400 prior to the onset of a surgical procedure based on the number of tracked uses, time being used, feedback of one or more electrical parameters, e.g., high current equating to excessive torque on cutting head during prior procedure, etc. This information may be relayed to the surgeon in any number of ways on the IPC 100 or may simply rate the condition of the disposable cutting tool 400 prior to use, e.g., from "good", to "fair", to "poor" and finally to "critical". This information may help the surgeon assess replacing the disposable cutting tool 400 prior to surgery even if the disposable cutting tool 400 has been verified or authenticated based on the number of times the disposable cutting tool has been used. For example, a disposable cutting tool 400 may have a use count of three (3) which is low for this particular disposable cutting tool 400 and cutting head 510 but have a "poor" rating based on a previous surgical use due to the shaft 512 becoming imbalanced or the cutting head 510 hitting a metal screw. The IPC 100 saved this important information in the cloud database to alert the surgeon prior to the next use.

While several aspects of the present disclosure have been shown in the drawings, it is not intended that the present disclosure be limited thereto, as it is intended that the present disclosure be as broad in scope as the art will allow and that the specification be read likewise. Therefore, the above description should not be construed as limiting, but merely as exemplifications of particular aspects. Those skilled in the art will envision other modifications within the scope and spirit of the claims appended hereto.

What is claimed is:

1. A surgical system for a cutting device, comprising:

an integrated power console (IPC) configured to power a motor of a cutting device and monitor feedback from at least one indicator during use over time to indicate the condition of the motor, the IPC including a database of disposable cutting tools and associated operating and safety parameters; and a disposable cutting tool operably connected to the IPC, the disposable cutting tool including an elongated shaft operably engageable within the cutting device and supporting a cutting head at a distal end thereof such that rotation of the elongated shaft and the cutting head cuts tissue or bone, the disposable cutting tool including:

a shaft assembly configured to operably engage and selectively lock the disposable cutting tool onto the cutting device;

a proximal connector configured to operably align and engage the elongated shaft of the disposable cutting tool with an output shaft of the motor; and an annular coupling disposed within the shaft assembly and configured to operably engage the shaft assembly and the proximal connector, at least a portion of an inner peripheral surface of the coupling made from a material configured to contact the elongated shaft such that upon engagement of the disposable cutting tool with the cutting device and during initialization, the IPC transmits and receives one or more electricals signals from the elongated shaft enabling the IPC to identify the disposable cutting tool from the database of disposable cutting tools and configure the associated operating and safety parameters particular to the disposable cutting tool, wherein a contact geometry of the inner peripheral surface of the coupling varies to create a unique electrical ID for each disposable cutting tool.

2. The surgical system according to claim 1, wherein the amount of material in contact with the elongated shaft varies to create the unique electrical ID for each disposable cutting tool.

3. The surgical system according to claim 1, wherein the type of material in contact with the elongated shaft varies to create the unique electrical ID for each disposable cutting tool.

4. The surgical system according to claim 1, wherein the contact geometry of the inner peripheral surface of the coupling includes a series of annular rings configured to create the unique electrical ID for each disposable cutting tool.

5. The surgical system according to claim 1, wherein the contact geometry of the inner peripheral surface of the coupling includes one or more flanges that extend along the coupling parallel to the elongated shaft to create the unique electrical ID for each disposable cutting tool.

6. The surgical system according to claim 5, wherein the one or more flanges comprises a plurality of flanges arranged 90° relative to one another.

7. A surgical system for a cutting device, comprising:

a disposable cutting tool including an elongated shaft having a proximal portion configured to operably engage the cutting device, the disposable cutting tool operably supporting a cutting head at a distal end thereof such that rotation of the elongated shaft and the cutting head cuts tissue or bone, the disposable cutting tool operably connected to an integrated power console (IPC) configured to power a motor to rotate the elongated shaft upon activation thereof and configured to monitor a condition of the motor via the elongated shaft, the IPC including a database of disposable cutting tools and associated operating and safety parameters, the proximal portion of the elongated shaft including a first geometric cross section, and the disposable cutting tool including:

a shaft assembly configured to operably engage and selectively lock the disposable cutting tool onto the cutting device;

a proximal connector configured to operably align and engage the elongated shaft of the disposable cutting tool with an output shaft of the motor; and an annular coupling disposed within the shaft assembly and configured to operably engage the shaft assembly and the proximal connector, at least a portion of an inner peripheral surface of the coupling including a second geometric cross section configured to complement and slidingly receive the first geometric cross section therein, such that upon engagement of the disposable cutting tool with the cutting device and during initialization, the IPC transmits and receives one or more electrical signals from the elongated shaft enabling the IPC to identify the disposable cutting tool from the database of disposable cutting tools and configure the associated operating and safety parameters particular to the disposable cutting tool.

8. The surgical system for a cutting device of claim 7, wherein the second geometric cross section of the coupling engages the first geometric cross section of the shaft in a fluid-tight sealing relation therewith.

9. The surgical system for a cutting device of claim 7, wherein a contact geometry of the inner peripheral surface of the coupling includes a series of annular rings.

10. The surgical system for a cutting device of claim 7, wherein a contact geometry of the inner peripheral surface of the coupling includes one or more flanges that extend along the coupling parallel to the elongated shaft.

11. The surgical system for a cutting device of claim 10, wherein the one or more flanges comprises a plurality of flanges arranged 90° relative to one another.

* * * * *